United States Patent [19]

Pohmer et al.

[11] Patent Number: 5,342,986
[45] Date of Patent: Aug. 30, 1994

[54] FLUORINATED CARBOXYLIC ACID ESTERS OF PHOSPHONOCARBOXYLIC ACIDS AND PHOSPHINOCARBOXYLIC ACIDS AND USE THEREOF

[75] Inventors: Klaus Pohmer, Köln; Rainer Weber, Odenthal; Hans-Dieter Block, Leverkusen; Cornelia Dörzhach-Lange, Körzbach-Bachen; Hans-Heinrich Moretto, Leverkusen, all of Fed. Rep. of Germany

[73] Assignee: Bayer AG, Leverkusen, Fed. Rep. of Germany

[21] Appl. No.: 157,820

[22] Filed: Nov. 24, 1993

[30] Foreign Application Priority Data

Dec. 9, 1992 [DE] Fed. Rep. of Germany ....... 4241478

[51] Int. Cl.$^5$ ............................ C07F 9/30; C07F 9/38
[52] U.S. Cl. ..................... 558/45; 558/44; 560/103; 560/105; 560/129; 560/195; 560/226; 560/227
[58] Field of Search .................. 558/45; 560/105, 129, 560/195, 227

[56] References Cited

U.S. PATENT DOCUMENTS

| | | | |
|---|---|---|---|
| 3,970,586 | 7/1976 | Schliebs et al. | 252/355 |
| 4,293,441 | 10/1981 | Newell et al. | 252/389 A |
| 4,602,092 | 7/1986 | Thottathil et al. | 560/105 |
| 4,740,608 | 4/1988 | Phillion | 558/45 |
| 4,776,875 | 10/1988 | Löher et al. | 560/129 |
| 4,824,886 | 4/1989 | Schmidt et al. | 524/131 |

FOREIGN PATENT DOCUMENTS

0238825  9/1987  European Pat. Off. .
2424243  11/1975  Fed. Rep. of Germany .

*Primary Examiner*—Jose'G. Dees
*Assistant Examiner*—Dwayne C. Jones
*Attorney, Agent, or Firm*—Connolly & Hutz

[57] ABSTRACT

The present invention relates to fluorinated carboxylic acid esters of phosphonocarboxylic acids or phosphinocarboxylic acids, and the use thereof as surface-active agents.

6 Claims, No Drawings

FLUORINATED CARBOXYLIC ACID ESTERS OF PHOSPHONOCARBOXYLIC ACIDS AND PHOSPHINOCARBOXYLIC ACIDS AND USE THEREOF

INTRODUCTION

The present invention relates to fluorinated carboxylic acid esters of phosphonocarboxylic acids or phosphinocarboxylic acids, and the use thereof as surface-active agents.

BACKGROUND OF THE INVENTION

As a result of their high degree of surface activity, perfluoroalkyl group-containing compounds have many uses in industry as fluoro-surfactants. Typical applications include utilization as cross-linking agents and emulsifiers and flow improvers in film coating, paints or dishwashing and cleaning agents (cf. "Ullmann, Enzyklopädie der technischen Chemie, 4th edition 1982, Vol. 22, p. 500"). Surface treatments and electroplating represent further areas in which they are utilized, for example to resolve wetting problems, reduce losses by entrainment and evaporation, and improve the surface finish (cf. "J. N. Meußdoerffer and H. Niederprüm, Chemikerzeitung 104 (1980), pp. 45–52").

Examples of such fluoro-surfactants are salts of perfluorocarboxylic acids or sulphonic acids and polyether-substituted perfluoroalkyl compounds (cf. "H. G. Klein, J. N. Meußdoerffer and H. Niederprüm, Metalloberfläche 29 (1975), pp. 559–567". "J. N. Meußdoerffer and H. Niederprüm, Chemikerzeitung 104 (1980, pp. 45–52" describes synthesis routes. The perfluorinated starting compounds for the aforementioned fluoro-surfactants are accessible industrially by three different synthesis routes:

a) electrochemical fluorination,
b) telomerisation of perfluoro olefines, in particular tetrafluoroethylene,
c) oligomerisation of tetrafluoroethylene.

Because the methods mentioned for preparing perfluorinated starting compounds use expensive technology, preparation of the perfluoro group-containing chemical compounds is very costly.

DETAILED DESCRIPTION OF THE INVENTION

The objective was to make available fluoro group-containing organo-modified surfactants which can be utilized as surface-active substances and which are easy and cheap to prepare.

This objective was achieved by the fluorinated carboxylic acid esters of phosphonocarboxylic acids and phosphinocarboxylic acids according to the invention.

The object of the invention is fluoroalkyl group-containing carboxylic acid esters of phosphonocarboxylic acids or phosphinocarboxylic acids of the general formula (I)

$$\begin{array}{c}R^1\phantom{xxx}O\\ \diagdown\parallel\\ P-Z-C-O-(CH_2)_n-(N)_m-Y_m-R_F,\\ \diagup\phantom{xx}\parallel\phantom{xxxxxxx}\mid\\ HO\phantom{xxx}O\phantom{xxxxxx}R_H\end{array} \quad (I)$$

wherein $R^1$ is a hydroxyl group, a methyl group, an ethyl group or a phenyl radical, $R_F$ is a branched or straight-chain fluoroalkyl radical having from 1 to 18 carbon atoms or a fluorinated, branched or straight-chain monoether or polyether having from 1 to 18 carbon atoms, $R_H$ is a branched or straight-chain alkyl radical having from 1 to 10 carbon atoms, Y denotes a $$\diagdown\phantom{xxx}\overset{O}{\underset{\parallel}{\phantom{x}}}\phantom{xxx}\overset{O}{\underset{\parallel}{\phantom{x}}}\phantom{xxx}\overset{O}{\underset{\parallel}{\phantom{x}}}\\ \phantom{xx}C=O, -S-, -O-S-, \text{ or } -O-C- \text{ group,}\\ \diagup\phantom{xxxx}\underset{\parallel}{\phantom{x}}\phantom{xxx}\underset{\parallel}{\phantom{x}}\\ \phantom{xxxxxxx}O\phantom{xxxx}O$$

Z stands for a straight or branched-chain alkylene radical having from 1 to 20 carbon atoms, or a straight or branched-chain alkylene radical having from 1 to 20 carbon atoms interrupted by amino groups which may themselves be substituted by $C_1$- to $C_{10}$-alkyl groups or aryl groups, or a straight or branched-chain alkylene radical having from 1 to 20 carbon atoms, which is substituted by one or more groups of the structure $-COR^2$, or a straight or branched-chain alkylene radical having from 1 to 20 carbon atoms, which is substituted by one or more groups of the structure $-PO_2HR^1$, wherein $R^1$ has the same meaning as above, m can be 0 or 1, n denotes an integer from 0 to 6 and $R^2$ stands for a hydroxyl radical or a radical of the structure $$-O-(CH_2)_n-(N)_m-Y_m-R_F,\\ \phantom{xxxxxxxxx}\mid\\ \phantom{xxxxxxxxx}R_H$$

or a straight or branched-chain alkoxy radical having from 1 to 20 carbon atoms, wherein n, m, $R_H$, $R_F$ and Y have the same meanings as above, and salts thereof.

Fluoroalkyl group-containing carboxylic acid esters of phosphonocarboxylic acids or phosphinocarboxylic acids are preferably those in which $R_F$ is a branched or straight-chain fluoroalkyl radical having from 3 to 10 carbon atoms.

Fluoroalkyl group-containing carboxylic acid esters of phosphonocarboxylic acids or phosphinocarboxylic acids in which $R_H$ stands for an alkyl radical having one or two carbon atoms are preferred.

Fluoroalkyl group-containing carboxylic acid esters of phosphonocarboxylic acids or phosphinocarboxylic acids in which n is one or two are particularly preferred.

Fluoroalkyl group-containing carboxylic acid esters of phosphonocarboxylic acids or phosphinocarboxylic acids in which m is one are particularly preferred.

Particularly preferred fluoroalkyl group-containing carboxylic acid esters of phosphonocarboxylic acids, for example, exhibit the following structures:

$$\begin{array}{c}HO\phantom{xxx}O\phantom{xxxxxxxxxxxxxxxxxxxxxxxxxx}O\\ \diagdown\parallel\phantom{xxxxxxxxxxxxxxxxxxxxxxxxxxxxxxxx}\parallel\\ P-CH_2-CH_2-C-O-CH_2-CH_2-N-S-C_4F_9\\ \diagup\phantom{xxxxxxxxxxxx}\parallel\phantom{xxxxxxxxx}\mid\phantom{x}\parallel\\ HO\phantom{xxxxxxxxxx}O\phantom{xxxxxxx}H_3C\phantom{x}O\end{array}$$

-continued

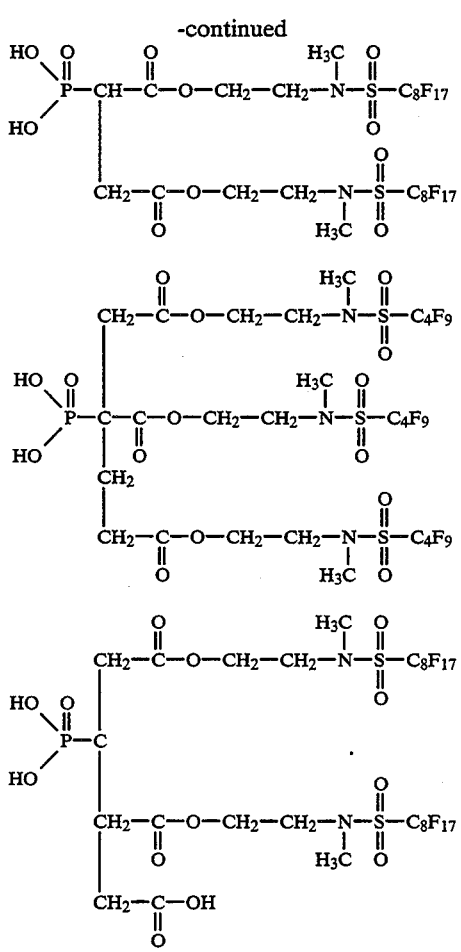

The radicals which appear in the following list are particularly preferred:

Examples of $R_F$

CF$_3$—(CF$_2$)$_2$—
CF$_3$—(CF$_2$)$_3$—
CF$_3$—(CF$_2$)$_5$—
CF$_3$—(CF$_2$)$_6$—
CF$_3$—(CF$_2$)$_7$—
CF$_3$—(CF$_2$)$_{11}$—
C$_6$F$_5$—
CF$_3$—C$_6$F$_4$—
H—(CF$_2$)$_6$—
H—(CF$_2$)$_2$—O—
CF$_3$—CHF—CF$_2$—O—
CF$_3$—CF$_2$—CF$_2$—O—CF(CF$_3$)—
CF$_3$—CF$_2$—[CF,$_2$—O—CF(CF$_3$)]$_2$—
CF$_3$—CF$_2$—[CF$_2$—O—CF(CF$_3$)]$_3$—

Examples of Z

—CH$_2$—, —CH(CH$_3$)—, —CH$_2$—, —CH$_2$CH$_2$—CH(CH$_3$)—,
—CH(CH$_3$)—CH$_2$—, —CH$_2$—CH$_2$—CH$_2$—, —CH(COOH)—CH$_2$—,
—CH$_2$—CH(CH$_2$—COOH)—, —CH(CH$_2$—CH$_2$—COOH)—CH$_2$—,
—CH[—CH(COOH)(PO$_3$H$_2$)]—, —CH(OH)—,
—C(CH$_2$—COOH)(CH$_2$—CH$_2$—COOH)—,
—C(CH$_2$—COOH)(CH$_2$—CH$_2$—PO$_3$H$_2$)—,
—C(CH$_2$—COOH)(—CH(COOH)—CH$_2$—COOH)—,
—CH(CH$_2$—CH$_2$(COOH)—,
—CH(CH$_2$—CH$_2$—PO$_3$H$_2$)—, —C(CH$_2$—CH$_2$—COOH)$_2$—,
—C(CH$_2$—CH$_2$—COOH)(CH$_2$)—CH$_2$—PO$_3$H$_2$)—,
—C(CH$_2$—CH$_2$—PO$_3$H$_2$)$_2$—,
—C(CH$_2$—COOH)(CH$_2$—CH$_2$—CN)—, —CH(CH$_2$—CH$_2$—CN)—,
—C(CH$_2$—CH$_2$—CN)$_2$—, —C(CH$_2$—$CH_2$—CN)(CH$_2$)—CH$_2$)—PO$_3$H$_2$) —,
—C(OH)(CH$_3$)—CH$_2$—, —C(OH)(CH$_3$)—CH$_2$—,
—C(OH)(CH$_3$)—CH(COOH)—CH$_2$—,
—CH$_2$—N(CH$_2$—PO$_3$H$_2$)—CH$_2$—, —CH$_2$—N(CH$_2$—COOH)—CH$_2$—,
—CH$_2$—NH—(CH$_2$—, —CH$_2$—NH—CH(CH$_3$)—,
—CH$_2$—$N(CH_2$—PO$_3$H$_2$)(CH(CH$_3$))—,

The fluoro group-containing carboxylic acid esters of phosphonocarboxylic acids or phosphinocarboxylic acids according to the invention can be prepared for example by single-stage synthesis in an esterification reaction between the corresponding phosphonocarboxylic acids or phosphinocarboxylic acids or salts thereof and fluoro group-containing alcohols:

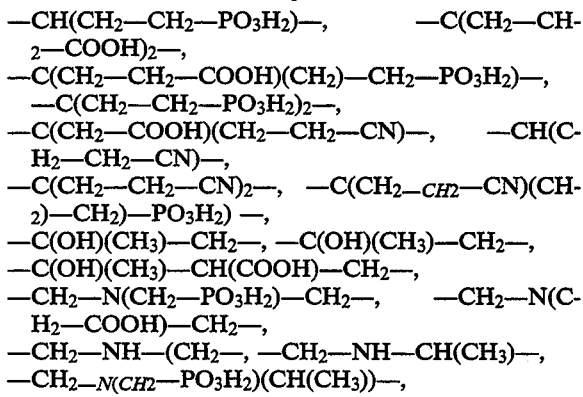

wherein $R_F$, $R_H$, Y, Z, m and n have the same meanings as above,

A is a hydrogen cation, an ammonium cation or a monovalent or multivalent metal cation, x is an integer corresponding to the charge of a cation A.

A further object of the invention is the use of the fluoroalkyl group-containing carboxylic esters of phosphonocarboxylic acids or phosphinocarboxylic acids as surface-active agents.

The high degree of surface activity of the fluoroalkyl group-containing carboxylic acid esters of phosphonocarboxylic acids or phosphinocarboxylic acids according to the invention enables them to act as highly efficient surfactants, making them utilizable, for example, in the following fields of application:

Electrolytic processes (for example for chromium, copper and nickel electroplating, anodising and electrolytic degreasing) wherein the compounds according to the invention may be added as spray suppressors and in order to prevent losses by entrainment.

Non-electrolytic bath processes (e.g. in chemical copper or nickel plating, chemical degreasing or rust removal, etching or engraving, immersion bright-coating, pickling, bronzing or passivation, anodic oxidation or stripping) wherein the compounds according to the invention may be added as spray suppressors and as aids to cleaning.

The compounds according to the invention may be added to cleaning agents and care products (for example, cleaning agents for glass, ovens, cars, buildings, facades or metal surfaces, stain removers, shampoos, polishes for use on furniture, cars etc., in self-shining emulsions or waxes), as flow improvers, spreading and cross-linking agents and to reinforce the properties which prevent resoiling.

The compounds according to the invention may be utilized as such, or they may be utilized in formulations as anti-deposit agents or to prevent bloom (for example on glasses, metals or plastics).

The compounds according to the invention may be utilised as such, or they may be utilized in formulations as corrosion inhibitors or anti-corrosion coatings (for example in polymerisation reactions, for fillers, fibres, salts or magnetic solids, in paints or in blood replacement products).

Because of their tendency to form gas-tight barrier layers and hence prevent evaporation of fluids, the compounds according to the invention are also suitable as fire extinguishant additives.

The compounds according to the invention may be utilized as mould lubricants.

Addition of the compounds according to the invention to paints and varnishes brings about improved flow, cross-linking and adhesion properties. They additionally prevent formation of surface defects (such as cratering or shrinkage away from the edges) by encouraging evacuation of air. Improved distribution of the pigments is furthermore achieved by their addition. The non-foam stabilising action of the compounds according to the invention is a particular advantage in recipes for preparing water-thinnable paints.

The tendency of the compounds according to the invention to form hydrophobic and oleophobic barrier layers enables them to be utilized in agents for protecting buildings (for example to insulate them from environmental influences).

The compounds according to the invention may be utilized as flow agents or slip agents (for example in mineral ores or mineral salts, on magnetic conveyors or in building materials).

The compounds according to the invention are suitable as lubricants, cutting oil additives or hydraulic oils.

The compounds according to the invention may be used as auxiliary substances for drilling (for example to increase oil drilling output).

The compounds according to the invention may be utilised in photographic chemicals or in film manufacture (for example as cross-linking agent or antistatic agent).

The compounds according to the invention may be utilized in plant protection products (for example as cross-linking agents and flow improvers).

Addition of the compounds according to the invention to textile, leather or paper finishing agents can, for example, promote the wetting or penetration of the finishing agent, bring about defoaming, or reinforce the hydrophobic/oleophobic action of the finishing agent.

The compounds according to the invention may be utilized as flameproofing agents (for example in plastics).

The compounds according to the invention may furthermore be utilized as liquid crystals.

The invention is explained in greater detail by means of the Examples which follow.

EXAMPLE 1

0.5 mole (178.5 g) of N-(2-hydroxyethyl)-N-methyl-perfluorobutyl sulphonamide is dissolved in 150 ml of 4-methylpentane-2-one in a three-necked flask with stirring apparatus and water separator, followed by addition of 0.5 ml concentrated sulphuric acid. This solution is heated to reflux (116° C). 0.5 mole (77 g) of 3-phosphonopropanoic acid is then slowly added under reflux. The temperature is held at reflux (100° C.) until all the water (0.5 mole) is distilled out of the reaction mixture and the temperature rises again to 116° C.

The solvent is then distilled out at 116° C., and the product obtained is dried at 50° C. and 50 mbar. The yield of the desired fluoro group-containing carboxylic acid ester of 3-phosphonopropanoic acid is 238.6 g (equivalent to 96.8% of theoretical yield). The surface tension of a 0.1% aqueous solution is 28.1 mN/m, and that of a corresponding 1% solution is 20.4 mN/m (measured with a ring tensiometer ex Lauda).

EXAMPLE 2

0.5 mole (278.5 g) of N-(2-hydroxyethyl)-N-methyl-perfluoro octyl sulphonamide is dissolved in 150 ml of 4-methylpentane-2-one in a three-necked flask with stirring apparatus and water separator, followed by addition of 0.5 ml concentrated sulphuric acid. This solution is heated to reflux (116° C.). 0.5 mole (77 g) of 3-phosphonopropanoic acid is then slowly added under reflux. The temperature is held at reflux (100° C.) until all the water (0.5 mole) is distilled out of the reaction mixture and the temperature rises again to 116° C.

The solvent is then distilled out at 116° C., and the product obtained is dried at 50° C. and 50 mbar. The yield of the desired fluoro group-containing carboxylic acid ester of 3-phosphonopropanoic acid is 342.2 g (equivalent to 98.8% of theoretical yield). The surface tension of a 0.1% aqueous solution is 31 mN/m (measured with a ring tensiometer ex Lauda).

EXAMPLE 3

0.4 mole (222.8 g) of N-(2-hydroxyethyl)-N-methyl-perfluoro octyl sulphonamide is dissolved in 150 ml of 4-methylpentane-2-one in a three-necked flask with stirring apparatus and water separator, followed by addition of 0.5 ml concentrated sulphuric acid. This solution is heated to reflux (116° C.). 0.2 mole (39.6 g) of phosphonoethane-1,2-dicarboxylic acid is then slowly added under reflux. The temperature is held at reflux (100° C.) until all the water (0.4 mole) is distilled out of the reaction mixture and the temperature rises again to 116° C.

The solvent is then distilled out at 116° C., and the product obtained is dried at 50° C. and 50 mbar. The yield of the desired fluoro group-containing carboxylic acid ester of phosphonoethane-1,2-dicarboxylic acid is 247 g (equivalent to 96.8% of theoretical yield). The surface tension of a 0.1% aqueous solution is 34.5 mN/m, and that of a corresponding 1% solution is 28.4 mN/m (measured with a ring tensiometer ex Lauda).

EXAMPLE 4

3.0 mole (1071 g) of N-(2-hydroxyethyl)-N-methyl-perfluorobutyl sulphonamide are dissolved in 850 ml of chlorobenzene in a three-necked flask with stirring apparatus and water separator, followed by addition of 3 ml concentrated sulphuric acid. This solution is heated to 120° C. 1.0 mole (54.0 g) of 2-phosphonobutane-1,2,4-tricarboxylic acid is then slowly added. When the addition is complete the temperature is held at reflux (100° C.) until all the water (0.6 mole) is distilled out of the reaction mixture and the temperature rises again to 116° C.

The solvent is then distilled out at 70° C., and at 70 mbar and the product obtained is dried completely. The yield of the desired fluoro group-containing carboxylic acid ester of 2-phosphonobutane-1,2,4-tricarboxylic acid is 1281 g (equivalent to 99.5% of theoretical yield).

The surface tension of a 0.1% aqueous solution is 22.4 mN/m (measured with a ring tensiometer ex Lauda).

EXAMPLE 5

0.4 mole (222.8 g) of N-(2-hydroxyethyl)-N-methyl-perfluoro octyl sulphonamide are dissolved in 150 ml of 4-methylpentane-2-one in a three-necked flask with stirring apparatus and water separator, followed by addition of 0.5 ml concentrated sulphuric acid. This solution is heated to reflux (116°C.) 0.2 mole (54 g) of 2-phosphonobutane-1,2,4-tricarboxylic acid is then slowly added under reflux. The temperature is held at reflux (100° C.) until all the water (0.4 mole) is distilled out of the reaction mixture and the temperature rises again to 116° C.

The solvent is then distilled out at 116° C, and the product obtained is dried at 50° C. and 50 mbar. The yield of the desired fluoro group-containing carboxylic acid ester of 2-phosphonobutane-1,2,4-tricarboxylic acid is 268 g (equivalent. to 99.4% of theoretical yield). The surface tension of a 0.1% aqueous solution is 28.2 mN/m, and that of a corresponding 1% solution is 27.6 mN/m (measured with a ring tensiometer ex Lauda).

WHAT IS CLAIMED IS:

1. Fluoroalkyl group-containing carboxylic acid esters of phosphonocarboxylic acids or phosphinocarboxylic acids of the general formula (I)

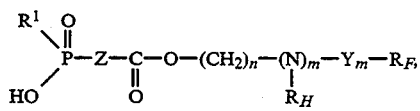

(I)

wherein
R$^1$ is a hydroxyl group, a methyl group, an ethyl group or a phenyl radical,
R$_F$ is a branched or straight-chain fluoroalkyl radical having from 1 to 18 carbon atoms or a fluorinated, branched or straight-chain monoether or polyether having from 1 to 18 carbon atoms,
R$_H$ is a branched or straight-chain alkyl radical having from 1 to 10 carbon atoms,
Y is a

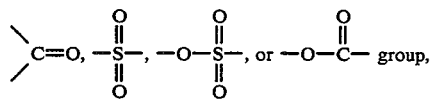

Z is a straight or branched-chain alkylene radical having from 1 to 20 carbon atoms, or a straight or branched-chain alkylene radical having from 1 to 20 carbon atoms interrupted by amino groups which may themselves be substituted by C$_1$- to C$_{10}$—alkyl groups or aryl groups, or a straight or branched-chain alkylene radical having from 1 to 20 carbon atoms, which is substituted by one or more groups of the structure -COR$^2$, or a straight or branched-chain alkylene radical having from 1 to 20 carbon atoms, which is substituted by one or more groups of the structure -PO$_3$HR$^1$, wherein R$^1$ has the same meaning as above,
m is 0 or 1,
n is an integer from 0 to 6 and
R$^2$ is a hydroxyl radical or a radical of the structure

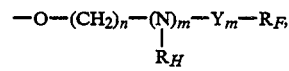

or a straight or branched-chain alkoxy radical having from 1 to 20 carbon atoms, wherein n, m, R$_H$, R$_F$ and Y have the same meanings as above, and salts of said fluoroalkyl group-containing carboxylic acid esters.

2. Fluoroalkyl group-containing carboxylic acid esters of phosphonocarboxylic acids or phosphinocarboxylic acids according to claim 1, wherein R$_F$ is a branched or straight-chain fluoroalkyl radical having from 3 to 10 carbon atoms.

3. Fluoroalkyl group-containing carboxylic acid esters of phosphonocarboxylic acids or phosphinocarboxylic acids according to claim 1, wherein R$_H$ is an alkyl radical having one or two carbon atoms.

4. Fluoroalkyl group-containing carboxylic acid esters of phosphonocarboxylic acids or phosphinocarboxylic acids according to claim 1, wherein n is one or two.

5. Fluoroalkyl group-containing carboxylic acid esters of phosphonocarboxylic acids or phosphinocarboxylic acids according to claim 1, wherein m is one.

6. Fluoroalkyl group-containing carboxylic acid esters according to claim wherein said esters have one of the following structures:

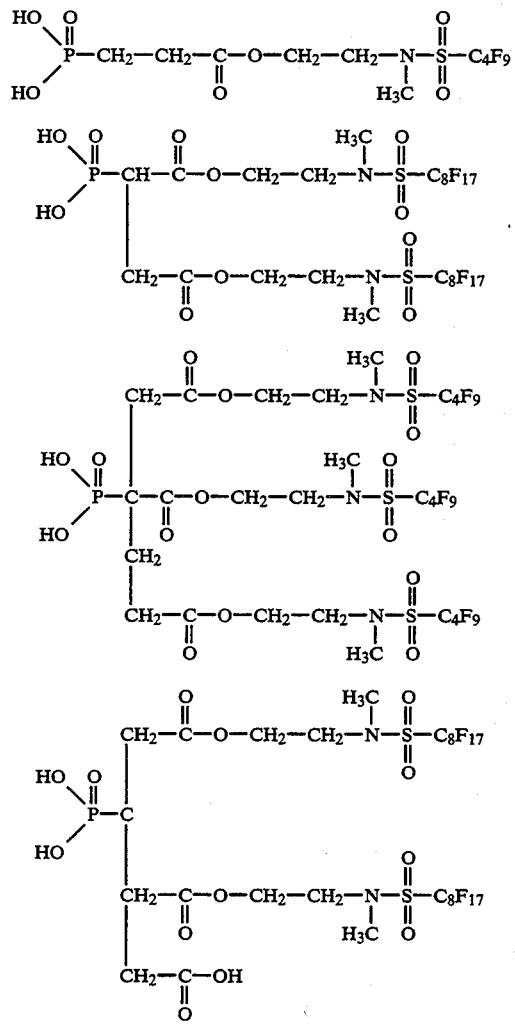

* * * * *

UNITED STATES PATENT AND TRADEMARK OFFICE
CERTIFICATE OF CORRECTION

PATENT NO. : 5,342,986
DATED : August 30, 1994
INVENTOR(S) : Klaus Pohmer, et al It is certified that error appears in the above-indentified patent and that said Letters Patent is hereby corrected as shown below:

Column 8, line 26, the words "according to claim wherein" should read --according to claim 1, wherein--.

Signed and Sealed this

Twenty-ninth Day of August, 1995

Attest:

BRUCE LEHMAN

*Attesting Officer*  *Commissioner of Patents and Trademarks*